(12) United States Patent
Clement et al.

(10) Patent No.: US 8,970,370 B2
(45) Date of Patent: Mar. 3, 2015

(54) METHOD AND SYSTEM TO CALIBRATE PHYSICAL DATA

(75) Inventors: Wesley J. Clement, Collierville, TN (US); Steven Tethrake, Collierville, TN (US); Steven Morrison, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 729 days.

(21) Appl. No.: 13/221,614

(22) Filed: Aug. 30, 2011

(65) Prior Publication Data

US 2013/0049958 A1    Feb. 28, 2013

(51) Int. Cl.
*G08B 21/00* (2006.01)
*G01D 18/00* (2006.01)

(52) U.S. Cl.
CPC ......... *G01D 18/00* (2013.01); *A61B 2560/0223* (2013.01)
USPC ....................... 340/540; 340/870.04; 340/501

(58) Field of Classification Search
CPC .................. G01K 15/005; G01K 15/00; G01J 2005/0048; A61B 2017/00725; G01F 1/6965; G01P 21/00; H01L 22/00; G01D 18/00
USPC .......... 340/540, 870.04, 501; 702/99; 73/766; 374/1, E15.001, E15.002
See application file for complete search history.

(56) References Cited

U.S. PATENT DOCUMENTS

| | | | | |
|---|---|---|---|---|
| 4,079,618 A | * | 3/1978 | King | 374/1 |
| 4,901,257 A | * | 2/1990 | Chang et al. | 702/99 |
| 5,095,453 A | * | 3/1992 | Pierson et al. | 702/99 |
| 5,678,923 A | * | 10/1997 | Germanow et al. | 374/1 |
| 6,973,413 B2 | * | 12/2005 | Hashemian | 702/183 |
| 7,507,019 B2 | * | 3/2009 | Price | 374/1 |
| 7,785,000 B2 | * | 8/2010 | James et al. | 374/1 |
| 2005/0015158 A1 | * | 1/2005 | Min | 700/1 |
| 2008/0177493 A1 | * | 7/2008 | Shumaker et al. | 702/99 |
| 2010/0007464 A1 | * | 1/2010 | McTigue | 340/10.1 |

* cited by examiner

*Primary Examiner* — Firmin Backer
*Assistant Examiner* — Nay Tun
(74) *Attorney, Agent, or Firm* — Sorell Lenna & Schmidt LLP (57) ABSTRACT

A system and method for calibrating physical data sensing devices with physical data control devices is disclosed. The system and method are particularly useful for calibrating physical data sensing devices that measure physical data at periodic intervals different from the periodic intervals in which the physical data control device measure the physical data. The system and method provide a quick and accurate calibration between devices sampling at different rates.

20 Claims, 6 Drawing Sheets

| Date at Analysis | |
|---|---|
| Dry-Well 9142 | |

| Data Start Time | 10:57:59 |
|---|---|
| Data End Time | 12:40:59 |
| Elapsed Time (hh:mm) | 01:43 |

| Number of Data Points | 78 |
|---|---|

| | Unit 1 Probe A | Unit 1 Probe B |
|---|---|---|
| Maximum Difference | 1.000 °C | 2.000 °C |
| Average Difference | 0.974 °C | 0.987 °C |
| Standard Deviation | 0.159 °C | 0.197 °C |

FIG. 4

| Time | Dry-Well 9142 Temp | Unit 1 Probe A Temp | Unit 1 Probe B Temp |
|---|---|---|---|
| 10:57:59 | 25 | 26 | 26 |
| 10:58:59 | 25 | 26 | 26 |
| 10:59:59 | 25 | 26 | 26 |
| 11:00:57 | 25 | 26 | 26 |
| 11:01:58 | 25 | 26 | 26 |
| 11:02:58 | 25 | 26 | 26 |
| 11:03:58 | 25 | 26 | 26 |
| 11:04:58 | 25 | 26 | 26 |
| 11:05:58 | 25 | 26 | 26 |
| 11:06:58 | 25 | 26 | 26 |
| 11:07:58 | 25 | 26 | 26 |
| 11:08:58 | 25 | 26 | 26 |
| 11:09:59 | 25 | 26 | 26 |
| 11:16:59 | 6 | 7 | 7 |
| 11:17:59 | 6 | 7 | 7 |
| 11:18:58 | 6 | 7 | 7 |
| 11:19:58 | 6 | 7 | 7 |
| 11:20:58 | 6 | 7 | 7 |
| 11:21:58 | 6 | 7 | 7 |
| 11:22:58 | 6 | 7 | 7 |
| 11:23:58 | 6 | 7 | 7 |
| 11:24:58 | 6 | 7 | 7 |
| 11:25:58 | 6 | 7 | 7 |
| 11:26:58 | 6 | 7 | 7 |
| 11:27:58 | 6 | 7 | 7 |
| 11:28:58 | 6 | 7 | 7 |
| 11:29:58 | 6 | 7 | 7 |
| 11:35:59 | 1 | 2 | 3 |
| 11:36:59 | 1 | 2 | 2 |
| 11:37:59 | 1 | 2 | 2 |
| 11:38:59 | 1 | 2 | 2 |
| 11:39:59 | 1 | 2 | 2 |
| 11:40:59 | 1 | 2 | 2 |
| 11:41:58 | 1 | 2 | 2 |
| 11:42:58 | 1 | 2 | 2 |
| 11:43:58 | 1 | 2 | 2 |
| 11:44:58 | 1 | 2 | 2 |
| 11:45:58 | 1 | 2 | 2 |
| 11:46:59 | 1 | 2 | 2 |
| 11:47:59 | 1 | 2 | 2 |
| 11:54:58 | 31 | 31 | 31 |
| 11:55:58 | 31 | 32 | 32 |
| 11:56:58 | 31 | 32 | 32 |
| 11:57:58 | 31 | 32 | 32 |
| 11:58:58 | 31 | 32 | 32 |
| 11:59:58 | 31 | 32 | 32 |
| 12:00:58 | 31 | 32 | 32 |
| 12:01:58 | 31 | 32 | 32 |
| 12:02:58 | 31 | 32 | 32 |
| 12:03:58 | 31 | 32 | 32 |
| 12:04:59 | 31 | 32 | 32 |
| 12:05:59 | 31 | 32 | 32 |
| 12:06:59 | 31 | 32 | 32 |
| 12:07:59 | 31 | 32 | 32 |
| 12:12:59 | 36 | 36 | 36 |
| 12:13:59 | 36 | 37 | 37 |
| 12:14:59 | 36 | 37 | 37 |
| 12:15:58 | 36 | 37 | 37 |
| 12:16:58 | 36 | 37 | 37 |
| 12:17:59 | 36 | 37 | 37 |
| 12:18:59 | 36 | 37 | 37 |
| 12:19:59 | 36 | 37 | 37 |
| 12:20:59 | 36 | 37 | 37 |
| 12:21:59 | 36 | 37 | 37 |
| 12:22:59 | 36 | 37 | 37 |
| 12:28:58 | 25 | 26 | 26 |
| 12:29:58 | 25 | 26 | 26 |
| 12:30:58 | 25 | 26 | 26 |
| 12:31:58 | 25 | 26 | 26 |
| 12:32:58 | 25 | 26 | 26 |
| 12:33:58 | 25 | 26 | 26 |
| 12:34:58 | 25 | 26 | 26 |
| 12:35:58 | 25 | 26 | 26 |
| 12:36:58 | 25 | 26 | 26 |
| 12:37:58 | 25 | 26 | 26 |
| 12:38:59 | 25 | 26 | 26 |
| 12:39:59 | 25 | 26 | 26 |
| 12:40:59 | 25 | 26 | 26 |
| 12:41:59 | 25 | 26 | 26 |

FIG. 5

METHOD AND SYSTEM TO CALIBRATE PHYSICAL DATA

BACKGROUND

There is a need to track medical devices from their base materials and manufacture to their use, as well as after use in a surgical setting. These include sterile and non-sterile medical devices. The medical devices may be biological materials that are intended for implantation into a patient, such as proteins, treated bone material or bone matrix material, and the like. Medical devices such as these must be stored in an area, whether it be an entire room or a small cabinet, that has precise physical parameter control, including control of temperature, pressure, humidity, and the like. Many regulatory agencies also require reporting of adverse events, such as when the temperature exceeds an acceptable level.

Other industries also utilize precise physical control over various parameters of processing. Examples include hospitals, fertility clinics that store embryos and unfertilized eggs, clean rooms in manufacturing facilities such as semiconductor manufacturing, and the like. Precise control requires periodic review and audits of the probes and sensors that are utilized to measure and report the physical parameter (temperature, pressure, humidity, etc.). These audits typically will involve calibrating the sensing devices against a control device that is known to accurately sense the physical parameter being calibrated. If the sensing devices deviate too far from the control sensor, then the sensing device that deviated must be serviced or replaced.

A problem arises when the control device samples at a rate that is different from the sampling rate of the sensing device (s) being calibrated. For example, the control device may sample every 5 seconds, whereas the device(s) being calibrated samples every 25 seconds, or every minute. Calibration of devices that sample at different rates typically requires manual inspection of the data and comparison of only the data points that were sampled at the same or similar interval(s). This is time consuming and can lead to errors in the comparison. There is therefore a need for a system and method for more reliably calibrating sensing devices in which the physical data are sampled at rates different from the control to which they are compared.

SUMMARY

Disclosed herein is a system and method for calibrating physical data obtained from sensing devices and control devices that sample at different rates. In accordance with one embodiment, there is provided a method that includes establishing set points for acceptable differences between baseline control data and comparison data, for differences between consecutive baseline data to accommodate ramping, establishing a least common sampling interval, and inputting those set points in a program stored on a computer readable medium. The method also includes retrieving baseline data from a data storage device and removing uncommon data from the data set that does not correspond to the least common sampling interval. The method includes comparing sequential data in the baseline data set and if consecutive data points differ by more than the established set point, the method removes the latest data point, and a predetermined number of data points to provide a baseline data set that includes common data. If there are no consecutive data points that differ by more than the established set point, then the data retrieved comprises the baseline data set after uncommon data has been removed.

The method also includes retrieving comparison data collected from the at least one device being compared to the baseline. The comparison data is retrieved from a storage device and is processed by optionally removing uncommon data from the comparison data to establish at least one comparison data set. The method then compares each common data point from the at least one comparison data set and the baseline data set, and if the difference between the compared data is greater than the established set point, the method alerts the user that the compared device has failed, and prints out a failure report indicating the failure and the differences between the data points. If the difference between the compared data is less than the established set point, the method provides a passing report and prints out a report indicating the differences between the data points.

In accordance with another feature of an embodiment, there is provided a system for automatically calibrating physical data obtained from sensing devices and control devices that sample at different rates. In accordance with this embodiment, there is provided at least one sensing device that senses physical data and provides comparison data to a storage device. The system further includes a control device that accurately measures physical data from a control sensing device and from at least one sensing device being calibrated, and provides baseline data to a storage device. The system also includes a storage device that communicates with the sensing device and the control device to store comparison data obtained from the at least one sensing device and to store baseline data obtained from the control sensing device. The system further includes a central processing unit having stored thereon a program and that is in communication with the storage device. The program stored on the central processing unit retrieves baseline data and comparison data from the storage device, manipulates the data by removing uncommon data and ramped data, and then compares the baseline data to the comparison data to determine the accuracy of the at least one sensing device.

The system and method described herein provides a fast and easy way to calibrate sensing devices that monitor physical data (e.g., temperature, pressure, humidity, etc.) in a controlled environment when the sensing devices sample the physical data at a rate different from the sampling rate of a control device. These and other aspects, forms, objects, features, and benefits of the present invention will become apparent from the following detailed drawings and description.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify the embodiments of this invention.

DETAILED DESCRIPTION

The present disclosure relates generally to the field of calibration of physical data sensors that sense physical data in controlled environments, and more particularly the field of calibration where the sensing devices sample at rates different from the sampling rate of the control device. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

The invention will be described with reference to a particularly preferred embodiment in which the sensing probe(s) sense the temperature of an RFID-enabled storage device or control room. RFID-enabled storage cabinets are known to store various types of materials, and some are designed to maintain the contents in a controlled temperature environment. This is particularly the case when the cabinets are used to store pharmaceuticals, biologic materials, certain medical devices, etc. Typically, the RFID-enabled storage cabinets have at least one temperature probe that monitors the temperature of the cabinet and is connected to a data collection system in which temperature is monitored in periodic intervals. If the temperature reaches a value outside an acceptable range, the RFID-enabled storage cabinets will present an alarm.

RFID-enabled cabinets provide inventory analysis of the cabinets to monitor inventory, monitor the healthcare providers who access the cabinets, what was removed and placed in the cabinet, etc. The RFID-enabled cabinets typically can be in communication with central servers or other storage devices (either directly via a LAN line or wirelessly) that may be accessible by multiple sources including device manufacturers, regulatory agencies, hospital administration, and the like. The RFID-enabled cabinets are capable of providing temperature and other related physical data (e.g., humidity, pressure, etc.) on a periodic basis for monitoring and reporting purposes.

Exemplary RFID-enabled cabinets are commercially available from Terso Solutions, which provide RFID-enabled cabinets, freezers and refrigerators. The cabinets are suitable for use in Hospitals, Research labs, Universities, Pharmacies, Dental offices, Police departments, Crime labs, Stock rooms, Medical Device Manufacturers, Medical Device distributors, and the like. Specific applications include the storage of Reagents, Pedigree bio-samples, Class II pharmaceuticals, Cardiovascular products, Orthopedic supplies, Hazardous materials, biologics, and the like. Suitable cabinets for use in the invention include, for example, Model TS030, and Model TS032, commercially available from Terso Solutions, Inc., Madison, Wis., SpaceTrax, available from Stanley Inner-Space, Grand Rapids, Mich., AccuCab2D, available form WinWare, Marietta, Ga., and other cabinets available from WaveMark, Inc., Littleton, Mass. (www.wavemark.net/website/documents/cabinetspecs.pdf). Those skilled in the art will recognize that the embodiments described herein can be used with any RFID-enabled cabinet, or any other cabinet or room that has certain physical parameters controlled and monitored (e.g., clean rooms, biologic storage facilities, large server farms, etc.).

The reporting requirements for cabinets storing medical supplies, devices, and especially biologic materials such as bone allograft products, are rigorous. The physical conditions of the cabinet in which the materials are stored must be monitored closely and any deviation from the physical conditions that could reasonably be expected to lead to a reportable adverse reaction for a tissue recipient must be reported to the American Association of Tissue Banks (see www.aatb.org). See also AATB, Guidance Document, Current Good Tissue Practice, No. 3, Jun. 27, 2006.

It is known in the art to use Dry-Well temperature calibrators to calibrate temperature probes and ensure their accuracy. Most Dry-Well temperature calibration devices are provided with National Institute of Standards and Technology (NIST)-traceable calibration, and most have software to allow the user to adjust set points and ramp rates, create a text file or other type of file containing the data from the calibration unit, and perform thermal switch testing and the like. Suitable Dry-Well temperature calibrators are commercially available from Hart Scientific, a division of Fluke Corporation, Everett, Wash. (Models 9100S, 9102S, 9103, 9140, Wika Alexander Wiegand, Klingenberg, Germany (Model CTD9300-650 and -165), Metrology Wells from Fluke Corporation, Everett, Wash., (Models 9142, 9143, 9144, 9170 series, etc.). Many other Dry-Wells and Metrology Dry Wells are known in the art and could be used in the present embodiments.

In accordance with one embodiment, there is provided a system for automatically calibrating physical data obtained from sensing devices and control devices that sample at different rates. In accordance with this embodiment, there is provided at least one sensing device that senses physical data and provides comparison data to a storage device. The system further includes a control device that accurately measures physical data from a control sensing device and from at least one sensing device being calibrated, and provides baseline data to a storage device. The system also includes a storage device that communicates with the sensing device and the control device to store comparison data obtained from the at least one sensing device and to store baseline data obtained from the control sensing device. The system further includes a central processing unit having stored thereon a program, the central processing unit being in communication with the storage device. The program stored on the central processing unit retrieves baseline data and comparison data from the storage device, manipulates the data by removing uncommon data and ramped (or transition) data, and then compares the baseline data to the comparison data to determine the accuracy of the at least one sensing device.

A particularly preferred system is a system that calibrates at least one temperature probe from a temperature-controlled, preferably RFID-enabled medical device storage cabinet. Such a preferred system is shown with reference to FIG. 1, in which a calibration system 100 is shown that is useful for calibrating temperature sensing probes for a medical device storage cabinets. As mentioned above, certain temperature controlled cabinets 10 must maintain the temperature within certain limits (e.g., between 1 and 37° C.) and if the temperature exceeds those limits, an alarm sounds and the event must be reported to a regulatory agency such as the AATB. The cabinet 10 therefore is equipped with one or more temperature sensing probes 27, 29 that can monitor the temperature over certain intervals, such as every minute, every second, every hour, etc. The temperature recorded by each probe 27, 29 typically is stored in a data file in a data storage unit 40, or server. Cabinet 10 is equipped with means for transmitting data to a data storage unit 40 via connection 150, such as wireless transmission, or transmission over a dedicated line. Data storage device 40 also is in communication with one or more terminals 30 via connection 350, again either via wireless transmission or via a dedicated line.

Figure 1:
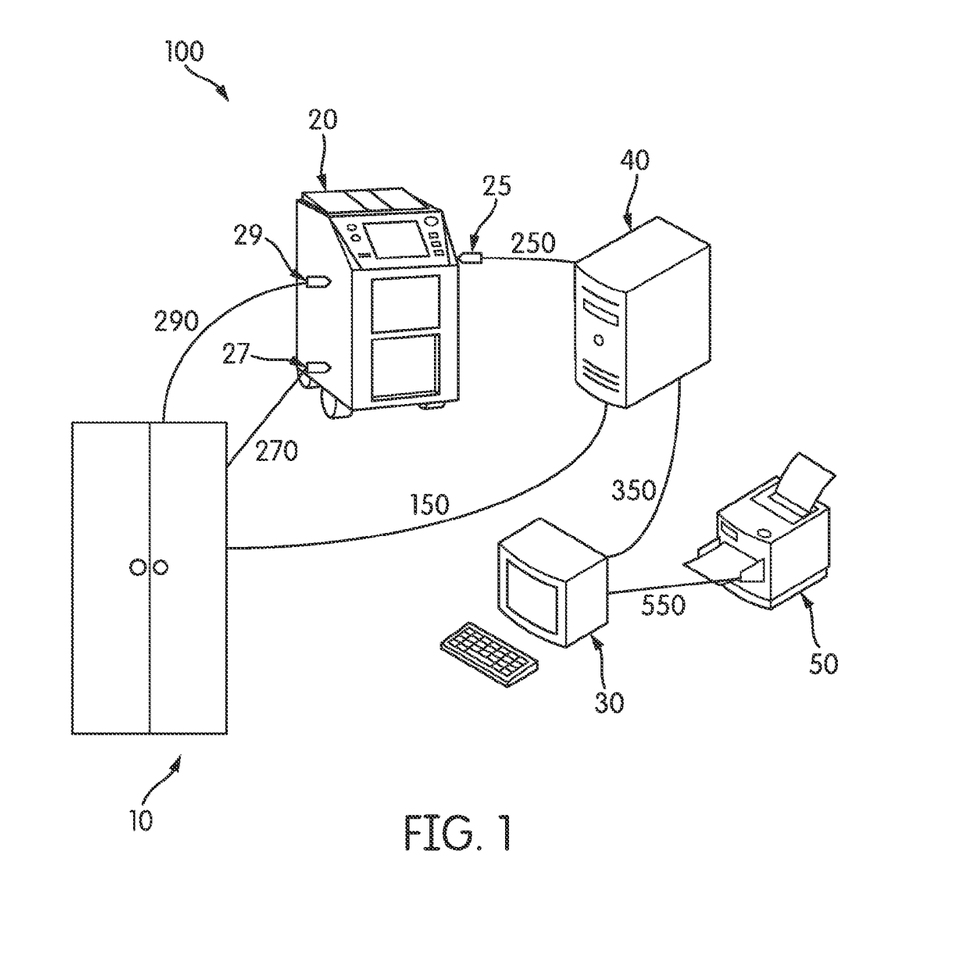
FIG. 1 is a view of a calibration system according to one preferred embodiment of the present disclosure.

The calibration system 100 is used when the temperature sensing probes 27, 29 are periodically audited to ensure their accuracy. To facilitate the calibration, a control device 20, such as a calibration dry well can be used to measure temperature from a control sensing device 25, or control temperature probe. While FIG. 1 shows control sensing device 25 outside the control device 20, it will be understood that the control sensing device 25 typically resides inside the control device 20. Control device 20 also preferably is equipped with means to input one or more sensing devices 27, 29 that are being calibrated. Some control devices 20 are equipped to calibrate multiple sensing devices, up to about 5 or more at a time.

Control device 20 can be any control device capable of accurately measuring and reporting physical data, and in the preferred embodiment, is a dry well or metrology well capable of accurately measuring temperature and calibrating multiple temperature probes at a time. A particularly preferred dry well used in a preferred embodiment is Metrology Well Model 9142, commercially available from Fluke Corporation, Everett, Wash. Control device 20 can be programmed to accommodate a number of sensing devices 27, 29 that are calibrated with control sensing device 25, and can be set to provide a number of different end points, with varying ramping speeds. For example, control device 20 can be adjusted to measure temperature within the range of 1 to 37° C., where the system might start at 25° C., then ramp down to 6° C. over a period of, say 2 seconds, and then hold at 6° for 10 minutes, then ramp down to 1° C., and hold, then ramp up to 31° C. and hold, then ramp up to 36° C. and hold, and then ramp back down to 25° C. and hold for one complete cycle. Those skilled in the art will be capable of setting end and hold points, ramp speeds, and other parameters, depending on the sensing devices 27, 29 to be calibrated. Control device 20 is equipped with means to output the precise physical data from control sensing device 25 to a data storage device 40 via connection 250, which can be a wireless or a physical connection.

Control device 20 typically measures the physical data at intervals that are not the same as the measuring interval provided by cabinet 10. Accordingly, the data stored in data storage device 40 for the sensing devices 27, 29 will contain data obtained at time intervals that do not necessarily correspond with the data stored in data storage device 40 for control sensing, which typically will have much more data collected in smaller intervals. By way of example, control device 20 may be equipped to provide temperature data from control sensing device 25 (or temperature probe 25) every 5 seconds, whereas cabinet 10 is equipped to provide temperature data from sensing devices 27, 29 (e.g., temperature probes) every minute, or every 30 seconds. In addition, because control device 20 provides data much more rapidly, it is highly likely that some of the data reported will be data obtained during one or more ramping periods in which the temperature were ramped up or down. These data will conflict with and likely provide an erroneous comparison when compared to the sensing devices 27, 29 being calibrated.

The system 100 described herein provides a fast and easy way to calibrate the data stored in data storage device 40 from the control sensing device 25, and from the sensing devices 27, 29 being calibrated. While FIG. 1 shows data storage device 40 being a separate device from terminal 30, data storage device 40 and terminal 30 may be the same device. The system enables calibration of the inconsistent data by providing a program on a computer readable medium in terminal 30. The program could be read from a computer readable medium, or stored in terminal 30, which could be a stand alone personal computer or laptop, or a networked device. Set points are initially established in the program for acceptable data deviations from the control sensing device 25, and acceptable deviations in data from consecutive data points from control sensing device 25. For example, industry standards may dictate that sensing devices 27, 29 cannot deviate by any more than 2° C. from control sensing device 25. Accordingly, the program stored on terminal 30 would be pre-set to indicate this as an acceptable set point. The program also would be set to filter out data from consecutive data points that deviate from one another by more than 1° C., for example, as this would indicate a ramping up or down of temperature. Finally, the program would be set to filter out the control device data that does not correspond to the data from cabinet 10 by filtering data that does not correspond to a least common sampling interval. For example, if cabinet 10 samples every minute, and control device 20 samples every second, or every 5 seconds, then the program would be set to filter out all data from control device 20 that did not correspond to the sampling rate of cabinet 10. This could be accomplished by eliminating or deleting all data from control device 20 other than data collected nearest to the minute. For example, if data from control device 20 were provided at 1:13:10, 1:13:35, and 1:13:59, the first two entries would be deleted and only the last entry would be saved.

After establishing the parameters for the program to run, the program then retrieves the control data from storage device 40, known as baseline data, and then modifies the baseline data to be consistent with the data from cabinet 10 by removing uncommon data and by accounting for ramps or transitions. The program therefore will establish a baseline data set, then retrieve the comparison data from storage device 40, which corresponds to the data collected from sensing devices 27, 29 and reported from cabinet 10 to storage device 40, and compare the comparison data set with the baseline data set. Because the program removed uncommon data from the baseline data set, the comparison is made at consistent intervals that correspond to the same time data was taken from the control sensing device 25, and the sensing devices 27, 29. If the comparison data deviates from the baseline data by more than the pre-determined set point, the system 100 will indicate a failure of the particular sensing device and a failure report could be generated at printer 50 via connection 550 with terminal 30. Alternatively, if the comparison data does not deviate from the baseline data by more than the pre-determined set point, the system 100 will provide a passing report, preferably at printer 50.

In accordance with another embodiment of the present invention, there is provided a method that includes establishing set points for acceptable differences between baseline control data and comparison data, for differences between consecutive baseline data to accommodate ramping, establishing a least common sampling interval, and inputting those set points and least common sampling interval in a program stored on a computer readable medium. The method also includes retrieving baseline data from a data storage device and removing uncommon data from the data set. The method includes comparing sequential data in the baseline data set and if consecutive data points differ by more than the established set point, the method removes the latest data point, and a predetermined number of data points to provide a baseline data set that includes common data. If there are no consecutive data points that differ by more than the established set point, then the data retrieved and modified to remove uncommon data comprises the baseline data set.

The method also includes retrieving comparison data collected from the at least one device being compared to the baseline. The comparison data is retrieved from a storage device and is processed by optionally removing uncommon data from the comparison data to establish at least one comparison data set. The method then compares each common data point from the at least one comparison data set and the baseline data set, and if the difference between the compared data is greater than the established set point, the method alerts the user that the compared device has failed, and optionally prints out a failure report indicating the failure and the differences between the data points. If the difference between the compared data is less than the established set point, the method optionally provides a passing report and prints out a report indicating the differences between the data points.

A particularly preferred method will be described with reference to FIGS. 2a and 2b. The method 600 enables calibration of sensing devices 27, 29 (or more sensing devices or just one sensing devices) when the control device 20 samples data at intervals that differ from the sampling rate of the sensing devices 27, 29. Method 600 operates in conjunction with system 100 depicted in FIG. 1, and preferably includes a program or other software that is either provided on a computer readable format (CD, DVD or other disc) or is stored in terminal 30 or on data storage device 40, or both if terminal 30 and data storage device 40 are integral with one another.

Figure 2A:
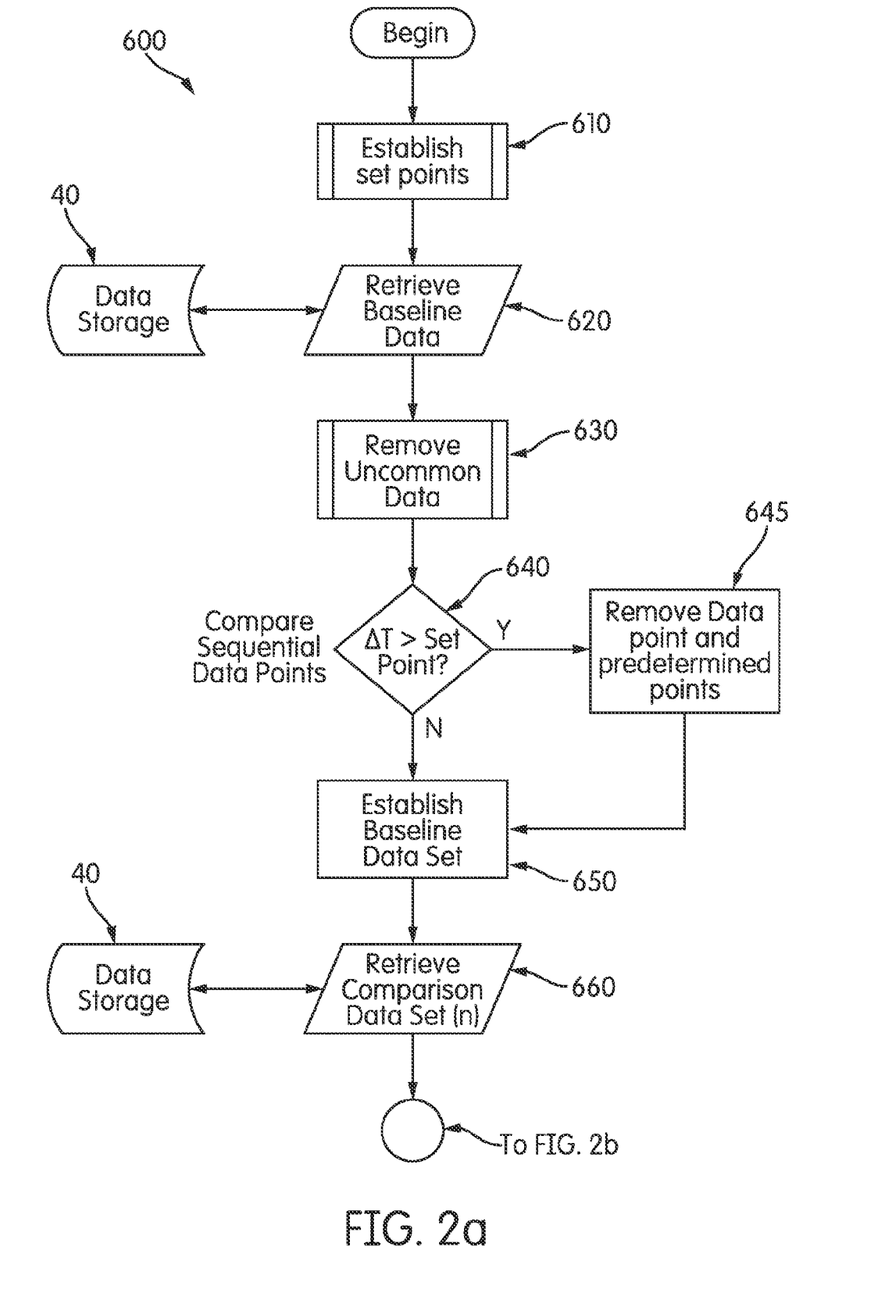
FIGS. 2a and 2b depict an exemplary flow chart for the method of a preferred embodiment of the invention.
Figure 2B:
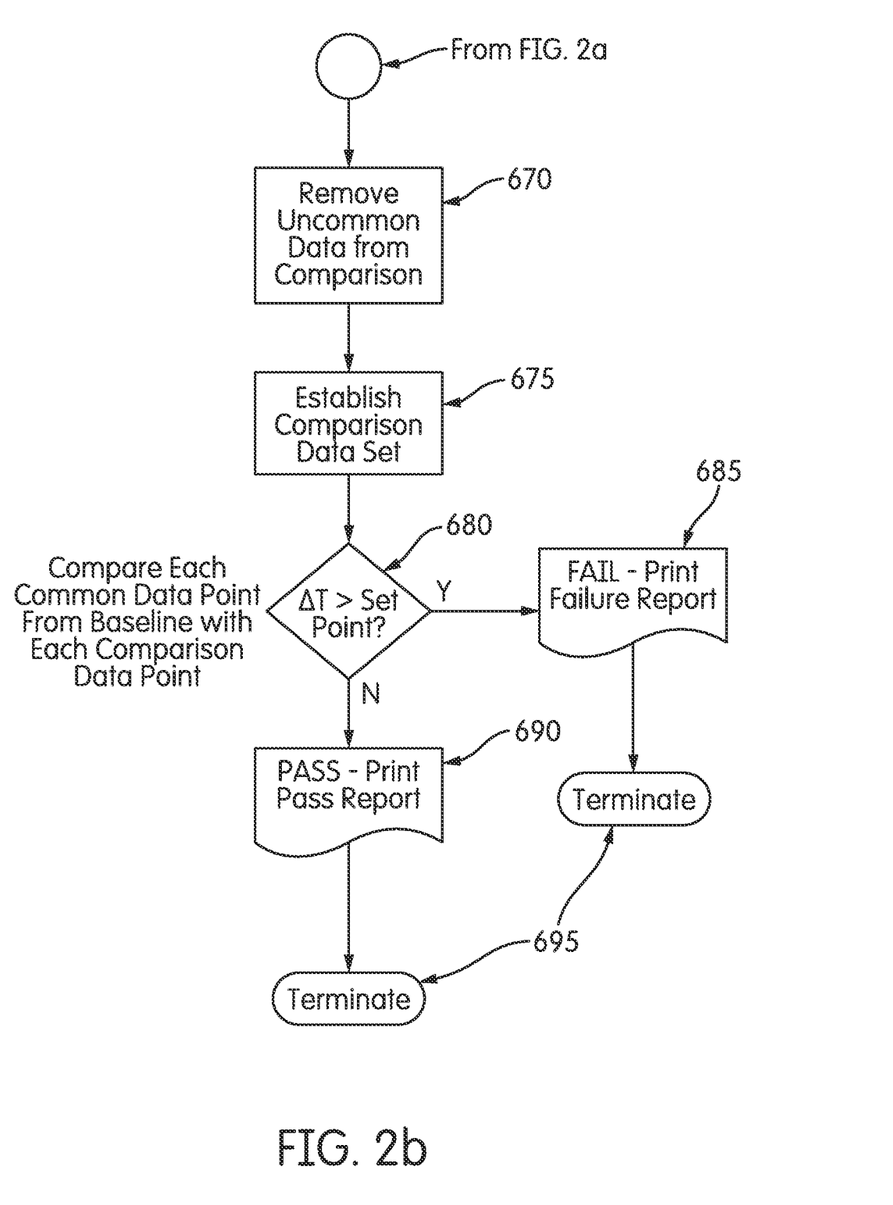

Referring now to FIGS. 2a and 2b, the method 600 includes establishing set points at 610 for acceptable differences between baseline control data and comparison data, and for differences between consecutive baseline data to accommodate ramping or transitions that occur in control device 20. Recall that control device 20 can be set prior to carrying out the calibration method 600 to provide a suitable number of end points, with varying ramping speeds. For example, control device 20 can be adjusted to measure temperature within the range of 1 to 37° C., where the system might start at 25° C., then ramp down to 6° C. over a period of, say 2 seconds, and then hold at 6° for 10 minutes, then ramp down to 1° C., and hold, then ramp up to 31° C. and hold, then ramp up to 36° C. and hold, and then ramp back down to 25° C. and hold for one complete cycle. Establishing the set points at 610 may include establishing a specific value for deviations between consecutive data points to eliminate the transitions or ramping. For example, if the temperature between consecutive data points from the baseline data set differ by more than 0.75° C., then this would be indicative of a transition or ramp from one temperature to another. Set point 0.75 then would be established at 610, and a predetermined number of data points also would be established at 610 to instruct the program to delete the last data point, and then 2, or 3, or 4, or whatever the pre-determined number of data points is from the baseline data set. A different set point also would be input at 610 that indicates an industry-acceptable standard for deviations from the control sensing device 25. This could be 2° C., for example. The final input at 610 would be the least common sampling interval from the control device 20 and the cabinet 10. For example, if cabinet 10 samples every minute, and control device 20 samples every 5 seconds, then the least common sampling interval would be one minute. This would be established at 610, or could be pre-determined in the software package.

Once the set points are established at 610, the method 600 then retrieves the baseline data at 620 from data storage device 40. The baseline data preferably is data collected from control device 20 as it relates to control sensing device 25. Once the baseline data is retrieved, the method removes uncommon data at 630. It is here where data from the baseline data is removed that does not correspond to the least common sampling interval. This could be accomplished by eliminating or deleting all data from control device 20 other than data collected nearest to the minute. For example, if data from control device 20 were provided at 1:13:10, 1:13:35, and 1:13:59, and the least common sampling interval were one minute, then the first two entries would be deleted and only the last entry would be saved. This would be completed for the entire data file to generate a new set of baseline data.

The method 600 then removes data from the baseline data that is believed to correspond to a transition or ramping up or down of the physical characteristic (e.g., temperature, pressure, etc.). Transition data likely would create a problem in comparing and generate a false reading of the calibration. As stated above, if the set point were established at 0.75° C., then at 640, the method would compare each consecutive data point with the previous data point and determine whether the difference exceeded the set point. Also established at 610 would have been the number of data points to remove in the event the difference exceeds the set point. In the preferred embodiment, this number could be 3 data points. Thus, at 640, the method compares each consecutive data point and if the difference is greater than the set point, then the last data point read, and three more consecutive data points would be removed from the baseline data at 645. If the difference calculated at 640 does not exceed the set point, then no data would be removed. After going through the comparison at 640, all transitions or ramps would be removed from the baseline data, and the method would establish a baseline data set at 650.

This baseline data set should contain data at intervals that correspond to the intervals present in the comparison data collected from the at least one device being calibrated. In the embodiment shown in FIG. 1, this would be the comparison data collected from sensing devices 27, 29, and recorded by cabinet 10 and reported as a data file to data storage device 40. Method 600 therefore continues by retrieving the comparison data at 660 from data storage device 40. Turning now to FIG. 2b, any uncommon data present in comparison data would be removed at 670. This would occur, for example, if the comparison data were collected every 30 seconds, and the baseline data were collected every 20 seconds. The least common interval would still be one minute intervals, and two data points would be removed from the baseline data at 630 (that correspond to sampling at 20 seconds and 40 seconds), and one data point would be removed from the comparison data at 670 (that corresponds to sampling at 30 seconds). In a preferred embodiment, no uncommon data would be removed from the comparison data. Removal of any uncommon data, if needed, establishes comparison data set at 675. Optionally, consecutive data points in the comparison data could be compared to delete transitions or ramps, in the same manner as discussed above with respect to the baseline data. For example, an additional comparison could be made on the comparison data similar to that made on the baseline data at 640, and transition or ramped data could be removed from the comparison data in a manner similar to that at 645. Carrying out the optional removal of uncommon data and the optional removal of transition data from the comparison data established the comparison data set at 675. The comparison data set established at 675 and the baseline data set established at 650 now should be directly comparable on the same intervals.

The calibration method 600 now can directly compare data from control sensing device 25 and sensing devices 27, 29 to be calibrated by comparing the baseline data set to the comparison data set. The acceptable maximum difference between the two data sets would be established as a set point at 610. Accordingly, at 680, the method compares each data point in the baseline data set with the corresponding data point in the comparison data set (or multiple comparison data sets if multiple sensing devices are being calibrated). If the maximum difference between any of the data points exceeds the set point, then the calibration would fail and the program will optionally generate a failure report at 685 and the method terminated at 695. If the maximum difference between any of the data points did not exceed the set point, then the calibration would pass, and an optional passing report would be generated at 690, and the method terminated at 695.

The method 600 can be used to calibrate one sensing device or multiple sensing devices, and can be used to calibrate sensing devices other than temperature probes. The method 600 and system 100 provide a fast and easy way to calibrate sensing devices against control devices when the sampling rates differ from one another. A particularly preferred method now will be described with reference to a calibration example carried out on an RFID-enabled temperature controlled medical device storage cabinet (referred to as a SmartStorage cabinet) with two temperature sensors. The temperature of the RFID-enabled cabinet has to be maintained with a temperature range of from 1 to 37° C., and the temperature probes cannot vary by more than 2° C. from the control, or the probe will fail calibration and will need to be serviced. The temperature sensing probes were calibrated in a metrology dry well, preferably Metrology Well Model 9142, commercially available from Fluke Corporation, Everett, Wash.

The Metrology dry well control device 20 was connected to a storage device 40, which may be separate from or integral with a terminal 30. Terminal 30 may be a personal computer loaded with software that is capable of carrying out the method described herein, or the software may be loaded on a disc read from terminal 30, or pre-loaded into data storage device 40. Alternatively, the software may be accessible wirelessly or through an internet connection to a remote server via a "cloud" computing connection. The dry well control device 20 was adjusted to measure various temperatures within the range of from 1 to 37° C., such that the well starts at ambient temperature, or 25° C. and is held there for about 12 minutes, then ramped down to 6° C. and held there for about 12 minutes, then ramped down to 1° C. and held there for about 12 minutes, then ramped up to 31° C. and held there for about 12 minutes, then ramped up to 36° C. and held there for about 10 minutes, and then ramped back down to 25° C. and held there for about 15 minutes. The entire cycle took about an hour and 43 minutes.

Two temperature sensing probes 27, 29 were input into the drywell control device 20, and the dry well control device was cycled through the above temperature fluctuations. Data collected from the drywell control sensing device 25 was provided as a data file to data storage unit 40, in which the data consists of temperature data collected every second over the hour and 43 minute cycle. Temperature sensing probes 27, 29 also had their data sensed and read by cabinet 10 and provided as a data file to data storage unit 40, in which the data consists of temperature data for each probe 27, 29, collected every minute over the hour and 43 minute cycle. Once both data files were stored in data storage device 40, the method 600 of the preferred embodiments was carried out.

Before carrying out the method, the program prompts the user at 610 to establish set points for consecutive temperature deviations, and for acceptable temperature deviations between the control device and the temperature probes 27, 29 being calibrated. In a particularly preferred embodiment, a user input 0.75° C. as an acceptable temperature deviation between consecutive data points, and 3 data points as a predetermined number of data points to remove if the consecutive data points exceeded the acceptable deviation. A user also preferably input 2° C. as an acceptable temperature deviation between the control device and the probes being calibrated. Finally, a user may input a least common sampling interval so that the method 600 will know what uncommon data to remove at 630 and optionally at 670. In this example, the least common interval was one minute.

The method then retrieved the data at 620 from control sensing device 25 in the form of baseline data that was stored in data storage device 40. Once the baseline data was retrieved, the method removed uncommon data at 630. It is here where data from the baseline data was removed that did not correspond to the least common sampling interval. This was accomplished by eliminating or deleting all data from the baseline data other than data collected nearest to the minute. In the preferred embodiment, only the last entry of each minute from the baseline data was saved—this entry would be at the final second of every minute. This was completed for the entire data file to generate a new set of baseline data.

The method 600 then removed data from the baseline data that was believed to correspond to a transition or ramping up or down of the physical characteristic (e.g., temperature, pressure, etc.). Transition data likely would create a problem in comparing and generate a false reading of the calibration. The set point was established at 610 as 0.75° C., then at 640, the method compared each consecutive data point (now only at one minute intervals because all other data from the baseline data were removed at 630) with the previous data point and determined whether the difference exceeded the set point. Also established at 610 was the number of data points to remove in the event the difference exceeds the set point, which in this embodiment was 3 data points. Thus, at 640, the method compared each consecutive data point and if the difference was greater than the set point, then the last data point read, and three more data points were removed from the baseline data at 645. The table below shows how the comparison was made and data points deleted:

Data Points Marked for Deletion

| Data Point | Time | Temperature |
| --- | --- | --- |
| 33 | 11:26:58 | 5.998 |
| 34 | 11:27:58 | 5.999 |
| 35 | 11:28:58 | 6 |
| 36 | 11:29:58 | 5.997 |
| 37 | 11:30:59 | 2.436 |
| 38 | 11:31:59 | 1.174 |
| 39 | 11:32:59 | 1.01 |
| 40 | 11:33:59 | 0.997 |
| 41 | 11:34:59 | 0.998 |
| 42 | 11:35:59 | 0.997 |
| 43 | 11:36:59 | 0.999 |
| 44 | 11:37:59 | 0.999 |
| 45 | 11:38:59 | 1.001 |

In the table above, the difference between data point 37 and 36 was greater than 0.75° C., thereby indicating a transition. Data point 37 therefore was removed, along with data points 38, 39, and 40 at 645. The difference between data point 38 and 37 also was greater than 0.75° C., thereby still indicating a transition. Accordingly, data point 38 was removed, along with data points 39, 40, and 41. Thus, by carrying out the comparison at 640, data points 37-41 were removed from the baseline data at 645.

If the difference calculated at 640 did not exceed the set point, then no data was removed. After going through the comparison at 640, all transitions or ramps were removed from the baseline data at 645 as described immediately above, and the method establishes a baseline data set at 650.

This baseline data set contained data at intervals that correspond to the intervals present in the comparison data collected from the at least one device being calibrated. Method 600 continued by retrieving the comparison data at 660 from data storage device 40. This data included the temperature data from temperature sensing probes 27 and 29. Optionally, any uncommon data present in comparison data would be removed at 670. This would occur, for example, if the comparison data were collected every 30 seconds, and the baseline data were collected every 20 seconds. The least common interval would still be one minute intervals, and two data points would be removed from the baseline data at 630 (that correspond to sampling at 20 seconds and 40 seconds), and one data point would be removed from the comparison data at 670 (that corresponds to sampling at 30 seconds). Optionally, any transition data also would be removed from the comparison data in the same manner described above with respect to the baseline data. In the particularly preferred embodiment described in this example, no uncommon data or transition data were removed from the comparison data. The comparison data set established at 675 and the baseline data set established at 650 now were directly comparable on the same intervals.

The calibration method 600 now directly compared data from drywell control device sensing probe 25 and RFID-enabled cabinet temperature sensing probes 27, 29. The acceptable maximum difference between the two data sets was established as a set point at 610 as 2° C. Accordingly, at 680, the method compared each data point in the baseline data set with the corresponding data point in the comparison data set (or multiple comparison data sets if multiple sensing devices are being calibrated). If the maximum difference between any of the data points exceeded the set point, then the calibration would have failed and a failure report optionally would have been generated at 685 and the method terminated at 695. The failure report would print out a table of temperature data and a summary page in which the probe that failed (or probes if multiple probes failed) could be highlighted in red. If the maximum difference between any of the data points did not exceed the set point, as was the case with the present example, then the calibration would pass, and a passing report was generated at 690, in which the summary data was printed in green to indicate a passing calibration, and the method terminated at 695.

Figure 3:
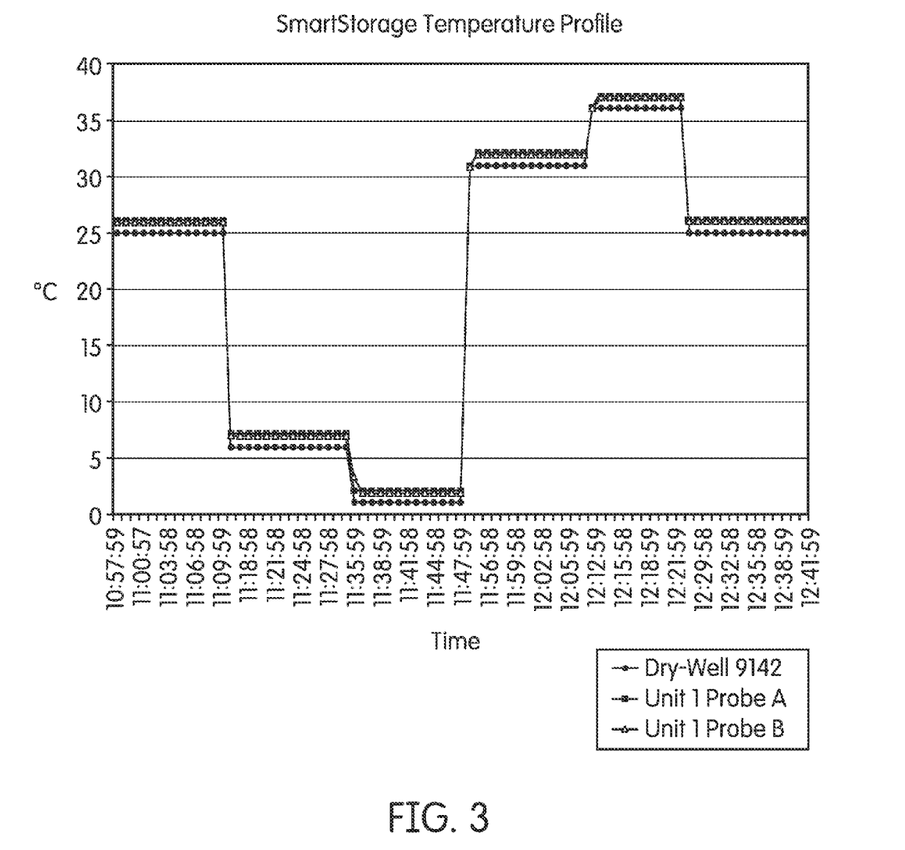
FIG. 3 is a temperature profile showing the comparison between a control temperature probe and two comparison temperature probes in accordance with a particularly preferred embodiment.
Figure 4:
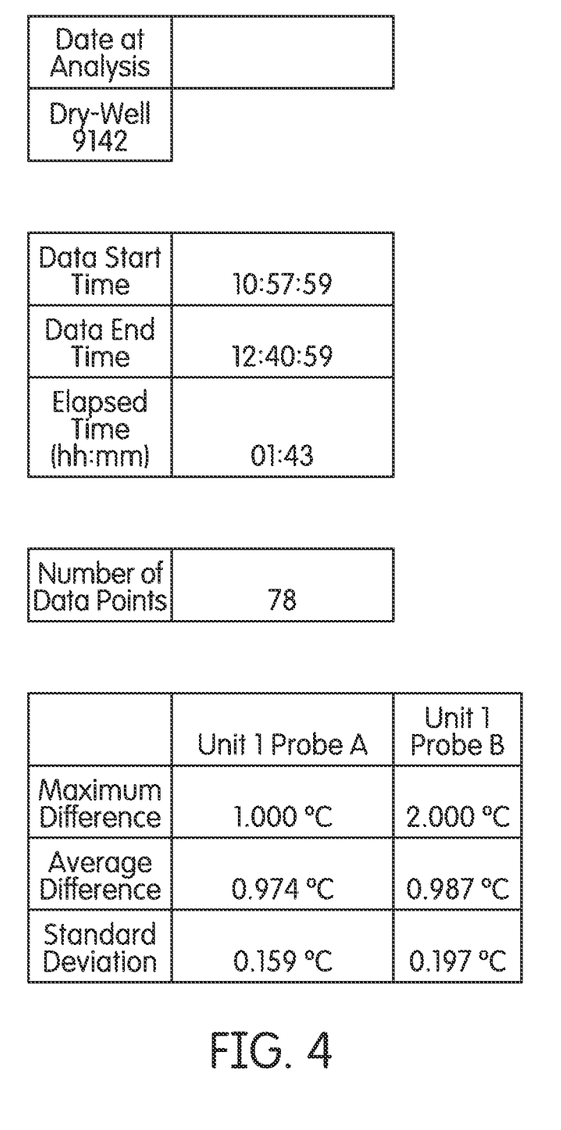
FIG. 4 is a summary print out of a chart showing the comparison between a control temperature probe and two comparison temperature probes shown graphically in FIG. 3.
Figure 5:
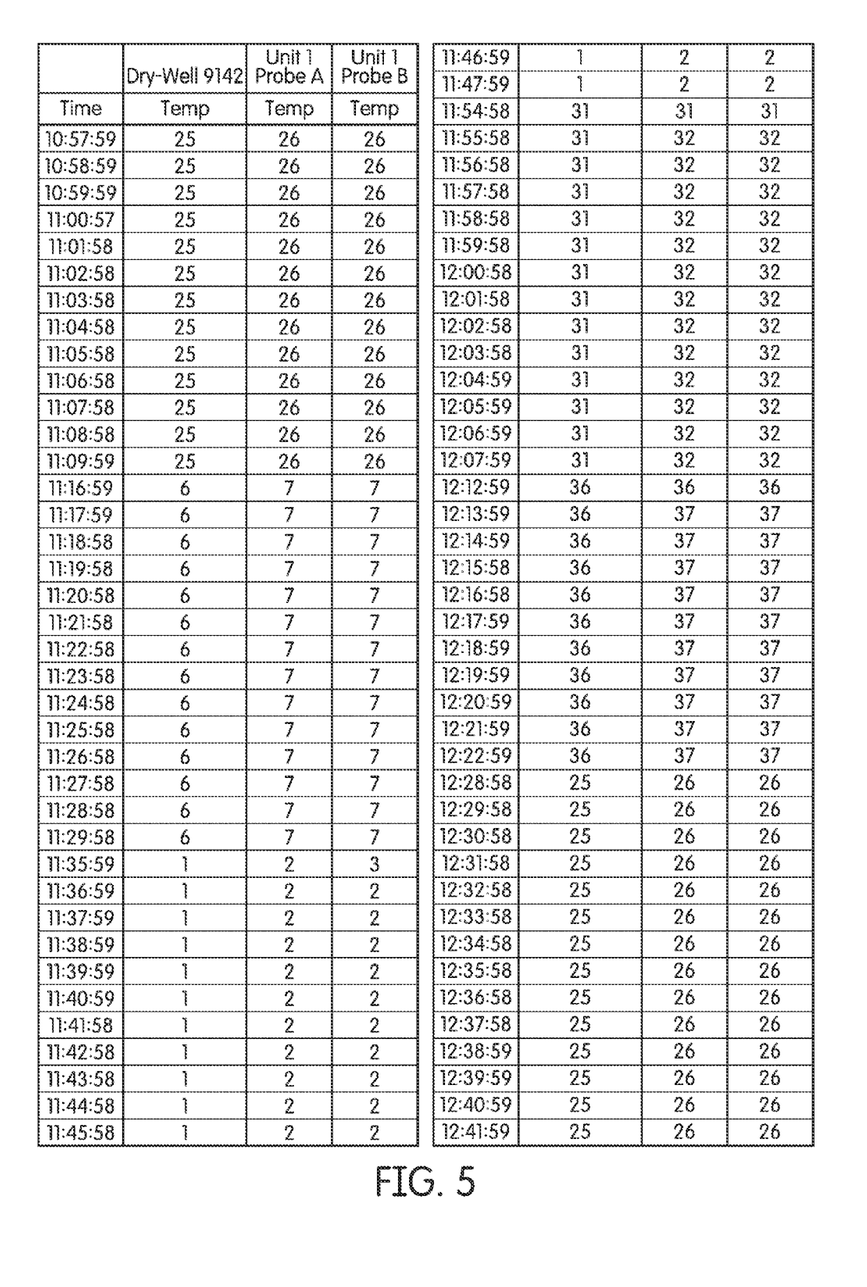
FIG. 5 is a print out of a chart showing the temperature comparison at common data points in accordance with the preferred embodiment shown graphically in FIG. 3.

FIGS. 3-5 are print-outs from a report generated when the above example was carried out. FIG. 3 shows the comparison between the baseline temperature data and the comparison temperature data. The baseline temperature was reported as dry well 9142 and is shown as a circle in the chart of FIG. 3. The first temperature sensor reported in the comparison data was Unit 1, Probe A and is shown by the square, and the second temperature sensor reported in the comparison data was Unit 1, Probe B and is shown by the triangle in FIG. 3. It is clear to see from FIG. 3 how the dry well control device maintained the temperature at certain values, then ramped the temperature up and down. One of those transitions was described above with reference to the removal of data if the comparison at 640 exceeded a set point, and shown in the table above. As described above, there was a transition recognized by the method at about 11:30 pm. FIG. 3 shows that at about this time, the dry well control device 20 was ramping down from 6° C. to 1° C.

FIG. 4 is a representative summary page from the report indicating that both temperature sensors, Probe A and Probe B, passed the calibration because neither had a maximum deviation of more than 2° C. The summary page shows that Probe B did have a maximum deviation of 2° C., which might be right on the edge of acceptability, thereby indicating a possible re-calibration or replacement of that particular probe. The summary page also provides the start and end times of the calibration run, the elapsed time (one hour and 43 minutes) and the number of data points compared (this should correspond to the number of data points present in the baseline data set after removal of uncommon data and transition data, as well as the number of data points present in the comparison data set).

FIG. 5 is a representative print out of the comparison made at 680, and provides temperature data at 79 data points (as shown in the summary of FIG. 4) for the dry well sensor, and for each probe (Probe A and Probe B). It can be seen that the transition data removed at 645 because of the comparison at 640 is not included in the data set.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

What is claimed is:
1. A method for calibrating a physical data sensing device with a physical data control device, in which the physical data sensing device and the physical data control device are sampled at different intervals, wherein the method is carried out by a program stored on a computer readable device, the method comprising:
   establishing a first set point for acceptable differences between baseline control data obtained from the physical data control device and comparison data obtained from the physical data sensing device;
   establishing a second set point for differences between the baseline control data obtained from the physical data control device to accommodate ramping, the baseline control data comprising consecutive data points;
   establishing a least common sampling interval between the physical data sensing device and the physical data control device;
   inputting the established first and second set points and the least common sampling interval into the program stored on the computer readable device;
   retrieving the baseline control data, the baseline control data being obtained from the physical data control device from a data storage device;
   removing uncommon data from the baseline control data by removing data that does not correspond to data collected at the least common sampling interval;

comparing sequential data in the baseline control data to determine if the consecutive data points differ by more than the second established set point;

removing the latest data point, and a predetermined number of sequential data points if the difference between sequential data points exceeds the second established set point, thereby providing a baseline control data set;

retrieving the comparison data obtained from the physical data sensing device from the data storage device to provide a comparison data set; and comparing the comparison data set with the baseline data set to determine if the maximum difference between the comparison data set and the baseline data set is greater than the first established set point, thereby calibrating the physical data sensing device with the physical data control device.

2. The method as claimed in claim 1, wherein the method provides an alert if the maximum difference between the comparison data set and the baseline data set is greater than the first established set point.

3. The method as claimed in claim 2, wherein the alert is in the form of a failure report indicating the physical data sensing device failed the calibration.

4. The method as claimed in claim 1, wherein the physical data sensing device is a probe capable of sensing physical data selected from the group consisting of temperature, pressure, humidity, and combinations thereof.

5. The method as claimed in claim 4, wherein the physical data sensing device is a temperature probe.

6. The method as claimed in claim 1, wherein the method provides a passing report if the maximum difference between the comparison data set and the baseline data set is less than the first established set point.

7. The method as claimed in claim 1, further comprising providing the baseline control data to the data storage device.

8. The method as claimed in claim 7, wherein providing the baseline control data is carried out by subjecting the physical data control device to various physical characteristics, measuring the physical characteristics at periodic intervals and providing data corresponding to the measured physical characteristic at each interval to the data storage device.

9. The method as claimed in claim 1, further comprising providing the comparison data to the data storage device.

10. The method as claimed in claim 9, wherein providing the comparison data is carried out by subjecting the physical data sensing device to various physical characteristics, measuring the physical characteristics at periodic intervals and providing data corresponding to the measured physical characteristic at each interval to the data storage device.

11. A system for automatically calibrating physical data obtained from sensing devices and control devices that sample at different rates, comprising:

a plurality of physical data sensing devices that each measure physical data and provide comparison data to a data storage device that corresponds to the physical data measured by each of the physical data sensing devices at intervals included in a first set of periodic intervals;

a control device that subjects the physical data sensing devices and a physical data control device to varying physical characteristics, that measures physical data from the physical data control device at intervals included in a second set of periodic intervals, and that provides baseline control data to the data storage device that corresponds to the physical data measured at each of the intervals in the second set of periodic intervals from the physical data control device, wherein the data storage device communicates with each of the physical data sensing devices and the control device to store the comparison data and the baseline control data;

a central processing unit integral with or in communication with the data storage device, the central processing unit having stored thereon a program;

wherein the program retrieves the baseline control data and the comparison data from the data storage device, manipulates the baseline control data by removing uncommon data and transition data from the baseline control data to provide a baseline data set, and then compares the baseline data set to the comparison data provided by each of the physical data sensing devices to determine the accuracy of the physical data sensing devices, thereby calibrating the physical data sensing devices, and wherein determining the accuracy of the physical sensing devices comprises determining if the comparison data provided by each of the physical data sensing devices deviates from the baseline data set by more than a selected amount for two or more intervals from the first set of periodic intervals.

12. The system as claimed in claim 11, wherein the physical data sensing devices are probes capable of sensing physical data selected from the group consisting of temperature, pressure, humidity, and combinations thereof.

13. The system as claimed in claim 12, wherein the physical data sensing devices are temperature probes.

14. The system as claimed in claim 11, wherein the physical data sensing devices are probes positioned within a storage cabinet.

15. The system as claimed in claim 14, wherein the storage cabinet is an RFID-enabled storage cabinet.

16. The system as claimed in claim 11, further comprising a printing device capable of printing a report generated by the program stored on the central processing unit.

17. The system as claimed in claim 11, wherein the plurality of physical data sensing devices includes two physical data sensing devices that are each calibrated with the physical data control device.

18. The method as claimed in claim 1, wherein the predetermined number of sequential data points is a number selected from a group consisting of two, three and four.

19. The method as claimed in claim 1, further comprising removing uncommon data from the comparison data by removing data that does not correspond to data collected at the least common sampling interval.

20. A method for calibrating a plurality of physical data sensing devices with a physical data control device, in which the physical data sensing devices and the physical data control device are sampled at different intervals, wherein the method is carried out by a program stored on a computer readable device, the method comprising:

establishing a first set point for acceptable differences between baseline control data obtained from the physical data control device and comparison data obtained from each of the physical data sensing devices at periodic intervals;

establishing a second set point for differences between the baseline control data obtained from the physical data control device to accommodate ramping, the differences between the consecutive baseline control data comprising consecutive data points;

establishing a least common sampling interval between each of the physical data sensing devices and the physical data control device;

inputting the established first and second set points and the least common sampling interval into the program stored on the computer readable device;

retrieving the baseline control data, the baseline control data being obtained from the physical data control device from a data storage device;

removing uncommon data from the baseline control data by removing data that does not correspond to data collected at the least common sampling interval;

comparing sequential data in the baseline control data to determine if the consecutive data points differ by more than the second established set point;

removing the latest data point, and a predetermined number of sequential data points if the difference between sequential data points exceeds the second established set point, thereby providing a baseline control data set;

retrieving the comparison data obtained from each of the physical data sensing devices from the data storage device to provide a plurality of comparison data sets; and comparing each of the comparison data sets with the baseline data set to determine if the maximum difference between each of the comparison data sets and the baseline data is greater than the first established set point for two or more of the periodic intervals, thereby calibrating the physical data sensing devices with the physical data control device.

* * * * *